US008350066B2

(12) United States Patent
Chami et al.

(10) Patent No.: US 8,350,066 B2
(45) Date of Patent: Jan. 8, 2013

(54) PROCESS FOR THE EXTRACTION OF BIOACTIVE LIGNANS WITH HIGH YIELD AND PURITY FROM SESAME OIL

(75) Inventors: Arumughan Chami, Kerala (IN); Chandrasekharan Pillai Balachandran, Kerala (IN); Mullan Velandy Reshma, Kerala (IN); Andikannu Sundaresan, Kerala (IN); Shiny Thomas, Kerala (IN); Divya Sukumar, Kerala (IN); Syamala Kumari Sathyanandan Saritha, Kerala (IN)

(73) Assignee: Council of Scientific & Industrial Design, New Delhi (IN)

( * ) Notice: Subject to any disclaimer, the term of this patent is extended or adjusted under 35 U.S.C. 154(b) by 321 days.

(21) Appl. No.: 12/570,428

(22) Filed: Sep. 30, 2009

(65) Prior Publication Data

US 2010/0204492 A1 Aug. 12, 2010

Related U.S. Application Data

(63) Continuation-in-part of application No. PCT/IN2008/000129, filed on Mar. 7, 2008.

(30) Foreign Application Priority Data

Mar. 30, 2007 (IN) ............................. 701/DEL/2007

(51) Int. Cl.
*C07D 307/00* (2006.01)
*C11B 5/00* (2006.01)

(52) U.S. Cl. ........................................ 549/435; 426/542

(58) Field of Classification Search .................. 549/435; 426/542
See application file for complete search history.

(56) References Cited

U.S. PATENT DOCUMENTS

| | | | | |
|---|---|---|---|---|
| 2,467,903 | A * | 4/1949 | Omohundro et al. | ......... 549/435 |
| 2,557,956 | A | 6/1951 | Feinstein et al. | |
| 2,786,063 | A | 3/1957 | Purdy et al. | |
| 2,837,534 | A | 6/1958 | Tracy | |
| 5,902,458 | A | 5/1999 | Sugiura et al. | |

OTHER PUBLICATIONS

Hemalatha Journal of American Oil and Chemical Society, 2004, 81(5)m 467-496.*

Hemalatha S; Ghafoorunissa: "Lignans and tocopherols in Indian sesame cultivars" Journal of the American Oil Chemists' Society, vol. 81, No. 5, May 2004, pp. 467-470, XP002493746 p. 467, right-hand column, paragraph 4.

Dachtler M; Van De Put F.H.M; V Stijn F; Beindorff C.M; Fritsche J: "On-line LC-NMR-MS characterization of sesame oil extracts and assessment of their antioxidant activity" European Journal of Lipid Science and Technology, vol. 105, No. 9, Sep. 2003, pp. 488-496, XP002493747 cited in the application p. 489, right-hand column, paragraph 2.

* cited by examiner

*Primary Examiner* — Nizal Chandrakumar
(74) *Attorney, Agent, or Firm* — Ladas & Parry LLP

(57) ABSTRACT

The present invention provides a process for the extraction and isolation of bioactive lignans with high yield and purity from Sesame oil by sequential extraction, crystallization, and saponification. The present invention provides a process for the production of highly pure bioactive lignan crystal, lignan enriched formulations with lignan content varying from 50 to 95% and with product flexibility and also at the same time preserve the starting raw material i.e. sesame oil.

13 Claims, No Drawings

PROCESS FOR THE EXTRACTION OF BIOACTIVE LIGNANS WITH HIGH YIELD AND PURITY FROM SESAME OIL

This application is a continuation-in-part of copending International Application IN2008/000129 filed on Mar. 7, 2008, which designated the U.S., claims the benefit thereof and incorporates the same by reference.

FIELD OF THE INVENTION

This invention relates to a process for the extraction of bioactive lignans with high yield and purity from Sesame oil.

BACKGROUND OF THE INVENTION

*Sesamum indicum* L is a domesticated crop and the most ancient oil seed known from Vedic times. It is grown primarily in the tropical and a subtropical region of the world. The world production of Sesame seed is approximately 3 million metric tones (MMT) and the Sesame oil availability is about 0.75 MMT. The major producers and processors of Sesame seed are India and China (25% each), Myanmar (10-13%), Sudan (10-12%), Japan (approximately 3%) etc. Though Japan is not a producer, it is a major importer (25%) and consumer, followed by European countries, USA and Canada. India and China are known for production, use and export of Sesame seed and its products. Traditional method of Sesame oil extraction in India was by ghani but commercial extraction now employs expeller, rotary, hydraulic press and solvent extraction of oil cake. Of the total production of Sesame oil (0.2 MMT), about 75% is used for edible. purpose, 5% for Vanaspathy industry and about 4% for industrial use as paints, soaps, perfumes etc. It has been known for many years that Sesame oil is highly resistant to oxidative deterioration as compared to other edible oils. This is attributed to the presence of biologically active compounds namely lignans and lignan glucosides. Lignans are a group of natural products of phenylpropanoid origin. The main lignans in Sesame oil are Sesamin and Sesamolin. Several food, industrial and pharmaceutical uses have been reported for these lignans. Studies have shown that Sesamin, the major compound present in Sesame inhibits cholesterol absorption and synthesis in rats. Both Sesamin and Sesamolin were reported to increase hepatic mitochondrial and peroxisomal fatty acid oxidation rate [J. B. Moriss In: Food, Industrial, Nutraceutical and Pharmaceutical Uses of Sesame Genetic Resources, Trends in New Crops and New Uses; pp 153-156, J. Janick and A. Whipkey (eds) ASHS Press; Alexandria, Va. (2002)]. Sesamin has also been known to modulate the PUFA pathways by inhibiting delta.sup.5-desaturase so that they produce less inflammatory mediators (Dachtler, M., Vande Put, F. H. M., Stijn, F: V., Beindorff, C. M and Fritsche, J., Eur. J. Lipid. Sci. Technol. 105,488-496,2003). Other benefits include lowering of serum triglycerides, reduction of high blood pressure, prevention of allergic reactions, enhancement of vitamin E activity, cancer prevention etc.

Lignans in Sesame oil is also reported to have antioxidant properties. Products of lipid oxidation are known to be health hazards since they are associated with ageing, membrane damage, heart disease and cancer (Cosgrove, J. P., Church, D. F and Pryor, W. A., Lipids, 22,299-304,1987). Lipid oxidation lowers-quality and nutritional value of foods. The addition of antioxidant is effective in retarding the oxidation of lipids and lipid containing foods. Synthetic antioxidants such as Butylated Hydroxy Anisole (BHA), Butylated Hydroxy Toluene (BHT) and Tertiary Butyl Hydroxy Quinone (TBHQ) are widely used in the food industry because they are effective and less expensive than natural antioxidant [Pin-Der, Duh and Gow-Chin, Yen., JAOCS, 74(6) 745-748,1997]. Their safety have been questioned(Chang et al, U.S. Pat. No. 5,043,100, 1991). This warrants for preparation and evaluation of natural antioxidants suitable for food and vegetable oil protection.

Antioxidant activity in Sesame cake extract have been studied in detail by various workers (Suja, K. P., John, T. A., Selvarn, N. T., Jayalekshmi, A and Arumughan, C., Food Chemistry, 84,393-400,2004; Suja, K. P., Jayaleksmi, A and Arumughan, C., Food Chemistry, 91,213-219,2005). It was found that antioxidant extract from Sesame cake at very low concentration can be substituted for synthetic antioxidants like BHT (Suja, K. P., Jayaleksmi, A and Arumughan, C., J. Agric. Fd. Chem, 52,912-915,2004, Suja, K. P., Jayaleksmi, A and Arumughan,C., J. Sci. Fd. Agric,85,1779-1783,2005).

Lignan in Sesame oil is reported to be in the range of 1 to 2% [Hemalatha, S and Ghafoorunissa, JAOCS, 81(5), 467-470, 2004]. Considering the bioactivity as cited above, Sesame lignans could be used as nutraceutical products. However an efficient process for commercial production has not been reported. The prior art on lignan extraction from Sesame oil is mostly patent related. Shinmen et al (U.S. Pat. No. 5,211,953, 1993) developed a liver function improver comprising, as an effective ingredient, a dioxabycyclo [3.3.0] octane derivative such as Sesamin and related compounds to a food or drink containing this derivative having a liver function improving action, a cholesterol level reducing action and/or a neutral fat level reducing action. An extract composed mainly of these compounds was obtained from Sesame oil by extraction with an immiscible organic solvent. The % yield of extract reported by methanolic extraction of oil was 2 to 3% based on start material. Dispersion of methanol extract in acetone, chilling, filtration and evaporation gave a compound specific extract with only 0.62% yield expressed on start material basis. They obtained a lignan content of only 32.23% in this extract based on total lignans in the oil, the start materiel. Alternatively they have tried super critical extraction of oil and also different chromatographic techniques for isolating desired lignan from the extract. However, the yield and purity of these compounds by these techniques have not been reported in this process. Namiki et al (U.S. Pat. No. 6,278;005, 2001) reported a process of producing Sesame lignans and/or Sesame flavours contained in the Sesame oil in higher purity and yield. In this process, Sesame oil was subjected to supercritical $CO_2$ extraction and the reported percentage yield of extracts ranged from 21-24%. The lignan content in the extract was only 1.5-3.5%. A composition for inhibiting delta.sup.5-desaturase consisting of lignan compounds, prepared for biopotency studies, by extracting Sesame seed or Sesame oil using organic solvents such as acetone, methyl ethyl ketone, diethyl ketone, methanol and ethanol has been patented by Akimoto et al (U.S. Pat. No. 5,336,496, 1994). Administering to animals, the composition showed inhibitory effects, which resulted in treatment of inflammation, thrombosis or hypertension? However, the yield and purity of the composition based on lignan content is not revealed in this process. The extraction of Sesame lignans from Sesame oil by liquid extraction with organic solvent followed by saponification and precipitation of the extract at 4° C. to obtain lignans have been reported by Dachtler et al (Euro. Lipid Sci. Technol, 105,488-496,2003). However the yield of extraction was very poor. Studies on the use of Sesame oil unsaponifiable matter (USM) as a natural antioxidant revealed that the USM possesses antioxidant properties with wide food application [Mohammed, H. M. A and Awatif, I. I., Food Chemistry, 62(3),269-276,1978]. They found that a combination of a number of minor constituents such as Tocopherol, Sesamol, Squalene and antipolymerization Sterols in the USM could have a synergistic role in increasing the oxidation stability of Sesame oil.

Most of the patents filed so far are related to preparation of lignan concentrate from Sesame oil for conducting studies on biological evaluation in animal models and human. Commercial and economic feasibility have not been addressed in terms of yield and purity in these patents. The present process reported here describes a most economical method to produce lignans with high yield and purity so that commercially the process is competitive in the international market.

OBJECTIVES OF THE INVENTION

The main objective of the present invention is to provide a process for extraction and iodation of bioactive lignans from Sesame oil with high yield and purity.

Another objective of the present invention is to provide a process for the production of bioactive lignan crystal with 50-60% yield and 90-95% purity.

Yet another objective of the present invention is to provide lignan crystals with lignan constituents comprising Sesamin from 70-85% and Sesamolin from 15-30%.

Yet another objective of the present invention is to preserve the starting material (>90%) i.e., Sesame oil, so that oil thus preserved could be used for edible/nonedible purpose.

Yet another objective of the present invention is to recover the residual lignans from the crystal removed methanolic concentrate by saponification followed by petroleum ether washing of the sesame oil unsaponiflable matters (USM) to obtain purified USM with 40-50% yield and 55-65% purity.

Yet another objective of the present invention is to provide USM with lignan constituents comprising Sesamin from 45-50% and Sesamolin from 50-55%.

Yet another objective of the present invention is to provide a bioactive lignan product with a product yield of 93-98% and with a purity of 75-80%.

Yet another objective of the present invention is to provide flexibility to produce range of products with varying lignan content through formulation of the said lignan products.

Still another objective of the present invention is to provide lignan products with other bioactive constituents like Phytosterol.

SUMMARY OF THE INVENTION

Accordingly the present invention provides a process for the extraction of bioactive lignans with high yield and purity from sesame oil and the said process comprising the steps of:

(a) subjecting the sesame oil to sequential extraction up to 6-10 times with methanol in a 1:1 to 1:1.2 portion (w/v), at a temperature in the range of 60 to 80 ° C., for a period of 60 to 100 minutes, with each extraction of 9 to 10 minutes duration and extracting the first and subsequent oil phase with a fresh methanol and preserving the oil phase separately after the last extraction, (b) concentrating the separated methanolid phase obtained from the above said sequential extractions, under vacuum and dispersing it in petroleum ether with a ratio of 1:0.4-1:0.6(v/v), (c) chilling the above said dispersion mixture, at a temperature of 4 to 10° C., for a period of 24 to 48 hours, followed by filtration and washing the resultant crystals with chilled petroleum ether till it gets free from oil and preserving the filtrate separately, (d) drying the above said resultant oil free crystals at a temperature less than 50° C., under vacuum, for a period of 30 to 60 minutes to obtain the desired bioactive pure lignan crystals, (e) desolventizing the filtrate obtained in step (c), under reduced pressure, to remove the petroleum ether and subjecting the resultant methanolic phase to saponification with 1:1 to 1:1.2 (v/v) of aqueous solution of potassium hydroxide (60:40, w/v) and 1:1 to 1:1.2 (v/v) of methanol or ethanol, for a period of 1 to 1.5 hours in a boiling water bath, adding water to the above said saponified resultant mixture in a ratio of 1:3-1:4 (v/v). Followed by extraction with petroleum ether in a ratio of 1:9-1:11 (v/v) for at least 6-8 times and each time separating the petroleum ether phase, (f) washing the separated petroleum ether extract obtained in step (e) with 10 to 12% methanol or ethanol till it gets free from alkali, concentrating the resultant extract under reduced pressure followed by drying at a temperature less than 60° C. to obtain the sesame oil unsaponifiable matters (USM), (g) washing the above said resultant USM with petroleum ether in a ratio of 1:0.6 to 1:0.7 (v/v) for 8 to 10 times to remove the impurities, followed by drying under vacuum, at a temperature lessthan 80° C. for 30 to 60 minutes to obtain the purified USM (h) admixing the above said purified USM obtained in step (g) with purelignan crystals obtained in step (d) to obtain the desired bioactive lignan enriched product.

In an embodiment of the present invention the oil phase separated in each extraction is subsequently extracted with fresh methanol.

In yet another embodiment the yield of extracted lignan content in methanolic concentrate in step (a) is 75-90% of the input lignan in the sesame oil.

In yet another embodiment the loss of sesame oil preserved in step (a) after subsequent methanolic extraction is 17-12%.

In yet another embodiment the ratio of methanolic extract to petroleum ether in a dispersion medium in step (b) is preferably 1:0.5 (w/v).

In yet another embodiment the yield of bio active lignan crystals obtained in step (d) is in the range of 50 to 60% of the input lignans in sesame oil.

In yet another embodiment the purity of the bio active lignan crystals obtained in step (d) is 90 to 95%.

In yet another embodiment the lignan crystals obtained in step (d) comprises 70-85% sesamin and 15-30% sesamolin.

In yet another embodiment the yield of lignans content of sesame oil USM is in the range of 40 to 50% of the input lignans in sesame oil.

In yet another embodiment the purity of the lignans content of sesame oil USM is in the range of 55-65% of the input lignans in sesame oil.

In yet another embodiment the yield of enriched bio active lignan product obtained in step (h) is 93 to 98% of the total input lignans in sesame oil.

In yet another embodiment the purity of enriched bioactive lignan product obtained in step (h) is 75 to 80%.

In still another embodiment the phytosterol content of sesame oil USM is in the range of 10 to 30% of sesame oil USM.

DETAIL DESCRIPTION OFTHE INVENTION

The following procedure has been developed for extraction and isolation of bioactive lignans from Sesame oil by sequential extraction, crystallization, and saponification. The sequential extraction is carried out in a three necked flask equipped with a motor driven stirrer, reflux condenser and thermometer assemblage. Sesame oil is charged into the flask and methanol is added in the specified proportion. The above mixture is stirred under reflux for the specified time duration at selected temperature. After the specified time of extraction, the mixture is allowed to settle for phase separation. The methanolic phase and oil phase are separately collected and oil phase is subjected for further sequential extraction under selected conditions of temperature and time. Time, temperature, solvent ratio and number of extractions have shown to effect lignan extraction from oil during the sequential step. Lignan recovery increased with extraction time at all temperatures with maximum recovery at 70° C. By changing the volume of solvent ratio, i.e., 1:2 and 1:0.5(w/v), no appreciable change in lignan extraction from that of 1:1 is noticed. Thus the solvent ratio is fixed as 1:1 at temperature 70° C.

The separated, pooled methanolic extract from the sequential extraction performed at 70° C., 1:1 solvent ratio is concentrated and dispersed in petroleum ether in the proportion 1:0.5 to facilitate crystallization. Dispersion volume of petroleum ether below and above 0.5 level was shown to affect the crystal yield adversely. Crystals are separated from the mixture by vacuum filtration followed by chilled petroleum ether washing till oil free and further drying in a vacuum oven at less than 60° C., yielded pure lignan crystals. The most significant finding is that, through crystallization step of the methanolic extract, 50-60% of lignans in the oil can be separated with high purity, with lignan constituents comprising Sesamin from 70-85% and Sesamolin from 15-30% according to HPLC analysis.

Also the resultant residual oil is preserved by desolventization to get the starting material, i.e., Sesame oil to the extent of 90%. Analytical results have shown that this resultant oil has residual lignan content 0.1 to 0.3%, bulk of the lignan in starting oil being extracted by methanol. Saponification studies of the crystal removed desolventized methanolic concentrate for different time duration reveal one hr saponification is sufficient to complete the reaction. Washing of the USM with chilled petroleum ether is found to increase the lignan content in the USM. HPLC analysis of the purified USM reveals that distribution of Sesamin and Sesamolin is in the range of 4:5 to 50% and 50 to 55% respectively unlike that Observed in the pure crystal. Alternatively, studies on the direct saponification of the methanolic concentrate d sequential extraction without the aforementioned, crystallization step reveal that USM with a lignan content of 70 to 75% according to HPLC analysis is also Obtained. HPLC analysis showed USM contained Phytosterols in addition to lignans in the range 20-30%; and the lignan products obtained by admixing contain 10-15% Phytosterols and the remaining being lignans.

The following examples are given by the way of illustration and therefore should not be construed to limit the scope of the invention.

EXAMPLE 1

100 g of commercial Sesame oil is sequentially extracted with 100 ml of methanol (w/v) in a three-necked flask equipped with motor driven stirrer, reflux condenser and thermometer assemblage in the following way. The temperature of extraction is maintained at 60° C. The mixture is continuously stirred at this temperature for 10 min and is allowed to settle. The separated methanolic and oil phases are collected and the residual oil phase so separated from the first sequential extraction is subjected to the second sequential extraction of 10 min duration with fresh batch of methanol in 1:1 proportion (w/v). The methanolic and oil phases from the second sequential extraction are separated and likewise sequential extraction is continued up to 100 min and separated methanolic phases are pooled. The pooled methanolic extract is concentrated under reduced pressure, in a flash evaporator and dried under vacuum at a temperature less than 60° C. The methanolic extract concentrate weighed 11.91 g and residual oil weighed 87.2 g.

EXAMPLE 2

HPLC analysis of the methanolic concentrate for lignans by reverse phase and quantitation of separated peaks is performed as follows. In an actual experiment, a Shimadzu make LC-10AD analytical HPLC equipped with Rheodyne injector fitted with 20 µl sample loop, a UV visible detector and C-R27Ae Model data analyzer is used. The column used is Luna 5µ C18 (2) (250×4.6 mm) and solvent system used is methanol: water (70:30 v/v) at a flow rate of 1 ml/min. The UV detector is set at 290 nm. Quantitation of separated peaks is done by calibrating with standard Sesamin (Sigma—Aldrich Co., USA). The peaks identified at RT—12.9 min is confirmed as Sesamin from coinjection of standard and that at RT 17.1 min is confirmed as Sesamolin based on earlier reports and is quantitated using response factor of Sesamin. On HPLC analysis, the extract showed a total lignan content of 0.91 g, the major lignan being Sesamin 0.64 g and Sesamolin 0.27 g.

EXAMPLE 3

100 g of commercial Sesame oil is sequentially extracted with 100 ml of methanol (w/v) in a three-necked flask equipped with motor driven stirrer, reflux condenser and thermometer assemblage in the following way. The temperature of extraction is maintained at 70° C. The mixture is continuously stirred at this temperature for 10 min and is allowed to settle. The separated methanolic and oil phases are collected and the residual oil phase so separated from the first sequential extraction is subjected to the second sequential extraction of 10 min duration with fresh batch of methanol in 1:1 proportion (w/v). The methanolic and oil phases from the second sequential extraction are separated and likewise sequential extraction is continued up to 100 min and separated methanolic phases are pooled. The pooled methanolic extract is concentrated under reduced pressure, in a flash evaporator and dried under vacuum at a temperature less than 60° C. The methanolic extract concentrate weighed 10.09 g and the residual oil weighed 89.2 g.

EXAMPLE 4

HPLC analysis of the methanolic concentrate for lignans is done as mentioned in example 2. On HPLC analysis the extract showed a total lignan content of 0.94 g, the lignan composition being Sesamin 0.66 g and Sesamolin 0.28 g.

EXAMPLE 5

1.00 g of commercial Sesame oil is sequentially extracted with 100 ml of methanol (w/v) in a three-necked flask equipped with motor driven stirrer, reflux condenser and thermometer assemblage in the following way. The temperature of extraction is maintained at 80° C. The mixture is continuously stirred at this temperature for 10 min and is allowed to settle. The separated methanolic and oil phases are collected and the residual oil phase so separated from the first sequential extraction is subjected to the second sequential extraction of 10 min duration with fresh batch of methanol in 1:1 proportion (w/v). The methanolic and oil phases from the second sequential extraction are separated and likewise sequential extraction is continued up to 100 min and separated methanolic phases are pooled. The pooled methanolic extract is concentrated under reduced pressure, in a flash evaporator and dried under vacuum at a temperature less than 60° C. The methanolic extract concentrate weighed 9.65 g and residual oil weighed 90.2 g.

EXAMPLE 6

HPLC analysis of the methanolic concentrate for lignans is done as mentioned in example 2. On HPLC analysis the extract showed a total lignan content of 0.85 g, the lignan composition being Sesamin 0.60 g and Sesamolin 0.25 g.

EXAMPLE 7

The above examples illustrated that maximum total lignan extraction is attained at an extraction temperature of 70° C.

EXAMPLE 8

1000 g of commercial Sesame oil is sequentially extracted with 1000 ml of methanol (w/v) in a three-necked flask equipped with motor driven stirrer, reflux condenser and thermometer assemblage in the following way. The temperature of extraction is maintained at 70° C. The mixture is continuously stirred at this temperature for 10 min and is allowed to settle. The separated methanolic and oil phases are collected and the residual oil phase so separated from the first sequential extraction is subjected to the second sequential extraction of 10 min duration with fresh batch of methanol in 1:1 proportion (w/v). The methanolic and oil phases from the second sequential extraction are separated and likewise sequential extraction is continued up to 100 min and separated methanolic phases are pooled. The pooled methanolic extract is concentrated under reduced pressure, in a flash evaporator and dried under vacuum at a temperature less than 60° C. The methanolic extract concentrate weighed 117.88 g and the residual oil weighed 880.0 g.

EXAMPLE 9

HPLC analysis of the methanolic concentrate for lignans is done as mentioned in example 2. On HPLC analysis the extract showed a total lignan content of 9.79 g, the lignan composition being Sesamin 6.85 g and Sesamolin 2.94 g.

EXAMPLE 10

The methanolic extract concentrate (117.88 g) as described in example 8 is dispersed in 59 ml petroleum ether (1:0.5 w/v) and the mixture is kept at low temperature 4 to 10° C. for 24 to 48 hrs to facilitate crystallization of the lignans. The crystals are separated from the mixture by vacuum filtration, washed with chilled petroleum ether till oil free, dried in a vacuum oven at temperature less than 60° C. for 30 min to 1 hr. The bioactive lignan crystal weighed 5.52 g.

EXAMPLE 11

HPLC analysis of the crystals showed 94.36% purity, the lignan composition being Sesamin 4.63 g and Sesamolin 0.89 g in the crystal mixture.

EXAMPLE 12

The filtrate after. crystal removal from example 10 is desolventized to remove petroleum ether by flash evaporation under reduced pressure. The resultant solvent stripped methanolic extract weighed 109.2 g. This desolventized methanolic extract is subjected to saponification by adding 109.2 ml (1:1 w/v) of Potassium hydroxide (KOH) in water (60:40 w/v) and 650 ml of ethanol (1:6 v/v) in a boiling water bath for 1 hr. After completion of saponification, 440 m1 of water (1:4 v/v) is added to the mixture and then extracted with 1:100 mil of petroleum ether (1:10 v/v) six times each time separating the petroleum ether phase. The separated petroleum ether fractions from the six extractions are pooled together and then washed with 10% ethanol till alkali free. The combined alkali free petroleum ether extract is flash evaporated under reduced pressure and then dried in vacuum oven at temperature less than 60° C. for 30 min to 1 hr to get the USM. The USM weighed 6.04 g.

EXAMPLE 13

HPLC analysis of the USM from example 12 for lignan content is done as mentioned in example 2. On HPLC analysis the USM showed 58.3% purity, the lignan composition being Sesamin 1.63 g, Sesamolin 1.89 g in the product.

EXAMPLE 14

HPLC analysis of the USM from example 12 for Sterol content is done by reverse phase and quantitation of separated peaks is performed as follows. In an actual experiment, a Shimadzu make LC-10AD analytical HPLC equipped with Rheodyne injectorfitted with 20 μl sample loop, a UV visible detector and C-R7Ae Model data analyzer is used. The column used is Zorbax ODS 5μ (250×4.6 mm) and solvent system used is methanol: water (96.5:3.5 v/v) at a flow rate of 1.2 ml/min. The UV detector is set at 206 nm. Quantitation of separated peaks is done by calibrating with standard Sterols (Stigmasterol, Campesterol, β-Sitosterol; Sigma—Aldrich Co., USA). The peaks identified at RT 30 min, 31 min and 34 min are confirmed as Stigmasterol, Campesterol and β-Sitosterol respectively by coinjection of standards and are quantitated using response factor of respective sterols. Total Phytosterol content of the USM is 28.04% according to HPLC analysis.

EXAMPLE 15

USM (6.04 g) from example 12 is washed with 4 ml petroleum ether (1:0.7 w/v) 10 times to remove the impurities. Petroleum ether washed USM, is dried in a vacuum oven at less than 60° C. for 30 min to 1 hr. The dried USM weighed 5.49 g.

EXAMPLE 16

HPLC analysis of the USM for lignans is done as mentioned in example 2. On HPLC analysis USM showed 63%. purity, the lignan composition being Sesamin 2.53 g and Sesamolin 2.97 g in the product.

EXAMPLE 17

Pure bioactive lignan crystal (5.52 g) obtained from example 10 is combined with the impurities removed USM from example 14 (5.49 g) to get the bioactive enriched lignan product. The enriched product weighed 11.01 g.

EXAMPLE 18

HPLC analysis of the enriched lignan product showed a purity of 78-80% with 93-98% product yield with respect to lignan content of Sesame oil.

EXAMPLE 19

The methanolic concentrate (10.09 g) from example 3 is subjected to saponification as mentioned in example 12. The USM weighed 0.93 g.

EXAMPLE 20

HPLC analysis of the USM (example 19) for lignan content is done as mentioned in example 2. On HPLC analysis the USM showed 73% purity, the lignan composition being Sesamin 80% and Sesamolin 20%.

EXAMPLE 21

HPLC analysis of the USM (example 19) for Sterol content is done as mentioned in example 14. Total Phytosterol content of the USM is 18.2% according to HPLC analysis.

Advantages:

The main advantages of the present invention are:

1. The development of process for the extraction of bioactive lignan from Sesame soil by sequential extraction with organic solvents such as alcohols whereby a ten told increase of lignan content is effected in methanol concentrate as compared to the starting material—Sesame oil.
2. After the extraction of bioactive lignans from oil, the starting material is preserved with loss of only 10% and the Sesame oil thus preserved (90%) could be used as edible oil to lower cost of production substantially.
3. By low temperature treatment of the methanolic extract, pure bioactive lignan crystals with a yield of 50 to 60% and a purity of 90 to 95%, enriched with Sesamin (70-80%) is obtained.
4. Simple step like saponification can be employed for the further recovery of remaining lignans from crystal removed methanol concentrate to get a yield of 40 to 50 USM % with 55 to 65% purity and with a different distribution profile of lignan constituents, i.e., Sesamin and Sesamolin.
5. Admixing of the crystals with USM can lead to another optional enriched lignan product with 93 to 98% yield and purity of 75 to 80%.
6. The process employs simple and less cumbersome procedures utilizing extraction and crystallization techniques, with saponification only as an additional step whereby making the process most economical and effective.
7. Direct saponification of methanolic concentrate after sequential extraction provides another versatile lignan enriched product with 70 to 75% lignan content.
8. The process can be employed for extraction and isolation of bioactive lignans from oil of different Sesame varieties.
9. The process provides flexibility to produce range of products with varying lignan content through formulations.
10. USM obtained by this process also contains bioactive Phytosterols.

The invention claimed is:

1. A process for the extraction of bioactive lignans from sesame oil wherein said process comprising the steps of:

(a) subjecting the sesame oil to sequential extraction up to 6-10 times with methanol in a 1:1 to 1:1.2 portion (w/v), at a temperature in the range of 60 to 80° C., for a period of 60 to 100 minutes, with each extraction of 9 to 10 minutes duration and extracting the first and subsequent oil phase with a fresh methanol and preserving the oil phase separately after the last extraction, (b) concentrating the separated methanolic phase obtained from the above said sequential extractions, under vacuum and dispersing it in petroleum ether in a ratio of 1:0.4-1:0.6 (v/v), (c) chilling the above said dispersion mixture, at a temperature of 4 to 10° C., for a period of 24 to 48 hours, followed by filtration and washing the resultant crystals with chilled petroleum ether till it gets free from oil and preserving the filtrate separately, (d) drying the above said resultant oil free crystals at a temperature less than 50° C., under vacuum, for a period of 30 to 60 minutes to obtain the desired bioactive pure lignan crystals, (e) desolventizing the filtrate obtained in step (c), under reduced pressure, to remove the petroleum ether and subjecting the resultant methanolic phase to saponification with 1:1 to 1:1.2 (v/v) of aqueous solution of potassium hydroxide (60:40, w/v) and 1:1 to 1:1.2 (v/v) of methanol or ethanol, for a period of 1 to 1.5 hours in a boiling water bath, adding water to the above said saponified resultant mixture in a ratio of 1:3 1:4 (v/v) followed by extraction with petroleum ether in a ratio of 1:9-1:11 (v/v) for at least 6-8 times and each time separating the petroleum ether phase, (f) washing the separated petroleum ether extract obtained in step (e) with 10 to 12% aqueous methanol or aqueous ethanol till it gets free from alkali, concentrating the resultant extract under reduced pressure followed by drying at a temperature less than 60° C. to obtain the sesame oil unsaponifiable matters (USM), (g) washing the above said resultant USM with petroleum ether in a ratio of 1:0.6 to 1:0.7 (v/v) for 8 to 10 times to remove impurities, followed by drying under vacuum, at a temperature less than 60° C. for 30 to 60 minutes to obtain the purified USM, (h) admixing the above said purified USM obtained in step (g) with pure lignan crystals obtained in step (d) to obtain the desired bioactive lignan enriched product.

2. The process according to claim 1, wherein the oil phase separated in each extraction is subsequently extracted with fresh methanol.

3. The process according to claim 1, wherein the yield of extracted lignan content in methanolic concentrate in step (a) is 75-90% of the input lignan in the sesame oil.

4. The process according to claim 1, wherein the loss of sesame oil preserved in step (a) after subsequent methanolic extraction is 7-12%.

5. The process according to claim 1, wherein the ratio of methanolic extract to petroleum ether in a dispersion medium in step (b) is preferably 1:0.5 (w/v).

6. The process according to claim 1, wherein the yield of bio active lignan crystals obtained in step (d) is in the range of 50 to 60% of the input lignans in sesame oil.

7. The process according to claim 1, wherein the purity of the bio active lignan crystals obtained in step (d) is 90 to 95%.

8. The process according to claim 1, wherein the lignan crystals obtained in step (d) comprises 70-85% sesamin and 15-30% sesamolin.

9. The process according to claim 1, wherein the yield of lignans content of sesame oil USM is in the range of 40 to 50% of the input lignans in sesame oil.

10. The process according to claim 1, wherein the purity of the lignans content of sesame oil USM is in the range of 55-65% of the input lignans in sesame oil.

11. The process according to claim 1, wherein the yield of enriched bio active lignan product obtained in step (h) is 93 to 98% product yield with respect to lignan content in methanol extract ,which accounts for 78-80% yield from Sesame oil.

12. The process according to claim 1, wherein the purity of enriched bio active lignan product obtained in step (h) is 75 to 80%.

13. The process according to claim 1, wherein the phytosterol content of sesame oil USM is in the range of 10 to 30% of sesame oil USM.

* * * * *

UNITED STATES PATENT AND TRADEMARK OFFICE

CERTIFICATE OF CORRECTION

PATENT NO. : 8,350,066 B2
APPLICATION NO. : 12/570428
DATED : January 8, 2013
INVENTOR(S) : Arumughan Chami et al.

It is certified that error appears in the above-identified patent and that said Letters Patent is hereby corrected as shown below:

Title Page, Item (73) Assignee: “Design” should read -- Research --.

Signed and Sealed this
Twenty-third Day of July, 2013

Teresa Stanek Rea
*Acting Director of the United States Patent and Trademark Office*